United States Patent
Stodilka et al.

(10) Patent No.: US 9,095,309 B2
(45) Date of Patent: Aug. 4, 2015

(54) METHOD AND APPARATUS FOR QUANTIFYING THE BEHAVIOR OF AN ADMINISTERED CONTRAST AGENT

(75) Inventors: Robert Z. Stodilka, London (CA); Frank S. Prato, London (CA)

(73) Assignee: Multi Magnetics Incorporated, London, Ontario (CA)

( * ) Notice: Subject to any disclaimer, the term of this patent is extended or adjusted under 35 U.S.C. 154(b) by 1100 days.

(21) Appl. No.: 12/210,430

(22) Filed: Sep. 15, 2008

(65) Prior Publication Data

US 2009/0124898 A1    May 14, 2009

Related U.S. Application Data (60) Provisional application No. 60/972,633, filed on Sep. 14, 2007.

(51) Int. Cl.
*A61B 5/055* (2006.01)
*A61B 6/00* (2006.01)
*A61B 6/03* (2006.01)

(52) U.S. Cl.
CPC ............ *A61B 6/507* (2013.01); *A61B 6/481* (2013.01); *A61B 6/504* (2013.01); *A61B 5/055* (2013.01); *A61B 6/037* (2013.01)

(58) Field of Classification Search
USPC .......... 600/407–480; 382/128, 130–134, 173, 382/174, 254–308, 318–321
See application file for complete search history.

(56) References Cited

U.S. PATENT DOCUMENTS

| | | | |
|---|---|---|---|
| 5,135,000 A | 8/1992 | Akselrod et al. | |
| 5,287,273 A | 2/1994 | Kupfer et al. | |
| 6,542,769 B2 | 4/2003 | Schwamm et al. | |
| 6,898,453 B2 | 5/2005 | Lee | |
| 2003/0097076 A1* | 5/2003 | Nambu et al. ................ | 600/504 |

OTHER PUBLICATIONS

Anderson, I.K. et al., "Perfusion Quantification Using Guassian Process Deconvolution", Magnetic Resonance in Medicine, pp. 351-361, 2002.

(Continued)

*Primary Examiner* — Mark Remaly
(74) *Attorney, Agent, or Firm* — Faegre Baker Daniels LLP (57) ABSTRACT

An apparatus for quantifying contrast agent behavior of an administrated contrast agent within a region of interest, comprises an imaging device configured to acquire images of a subject and processing structure communicating with the imaging device. The processing structure is configured to process image data of the acquired images to yield a time sequence of images, I(t), at a location (I) outside of the region of interest that detect contrast agent concentration before the contrast agent enters the region of interest and to yield a time sequence of images, J(t), at a location (J) within the region of interest that detect the contrast agent concentration as the contrast agent perfuses the region of interest. The processing structure is further configured to deconvolve I(t) from J(t) to determine a vector describing the time estimate of the impulse response function, R'(t), for the region of interest, where the shape of the vector is constrained using physiologic and physical considerations and $I(t) \otimes R'(t)$ is the maximum likelihood estimate of J(t), where $\otimes$ denotes convolution, and configured to determine the behaviour of the contrast agent in the region of interest based on the determined vector.

12 Claims, 4 Drawing Sheets

(56) References Cited

OTHER PUBLICATIONS

Mor-Avi, Victor et al., "Myocardial Transit Time of the Echocardiographic Contrast Media". Ultrasound in Med. & Biol., vol. 19, No. 8, pp. 635-648, 1993.

Jerosch-Herold, Michael et al., "Myocardial blood flow quantification with MRI by model-independent deconvolution", Med. Phys, 29 (5), May 2002.

Bammer, Roland et al., "Foundations of Advanced Magnetic Resonance Imaging", vol. 2, pp. 167-196, The American Society for Experimental NeuroTherapeutics, Inc., Apr. 2005.

Search Report dated Mar. 6, 2009 in corresponding European Application No. 08253027.0.

* cited by examiner

METHOD AND APPARATUS FOR QUANTIFYING THE BEHAVIOR OF AN ADMINISTERED CONTRAST AGENT

RELATED APPLICATIONS

This application claims the benefit of U.S. Provisional Application No. 60/972,633 to Stodilka et al. filed on Sep. 14, 2007, the content of which is incorporated herein by reference.

FIELD OF THE INVENTION

The present invention relates generally to medical imaging and in particular, to a method and apparatus for quantifying the behaviour of a contrast agent administered to a subject.

BACKGROUND OF THE INVENTION

Contrast agent kinetics is the study of the change of contrast agent concentration as a function of time, as the contrast agent enters into and perfuses a tissue of interest. Contrast agent kinetic analysis has applications in medical diagnostics by helping to characterize the functional state of a tissue, and applications in drug discovery by offering insight into the behavior of the contrast agent itself. Contrast agent kinetic analysis is used often in conjunction with an imaging device that can measure non-invasively, the concentration of the contrast agent, at one or more locations, as a function of time.

The fundamental behavior of a contrast agent in a tissue is quantified by the tissue impulse response function, $R(t)$. The tissue impulse response function $R(t)$ represents the temporal evolution of contrast agent concentration within a tissue if an ideal bolus, a Dirac delta function, of contrast agent had entered into that tissue without delay as described by Bassingthwaighte et al. in "Modeling in the analysis of solute and water exchange in the microvasculature", Handbook of Physiology Section 2: The Cardiovascular System ed Renkin E and Geiger S (Bethesda Md.: American Physiological Society) 549-626, 1984. The tissue impulse response function $R(t)$ is a function of both the contrast agent properties and the underlying tissue properties, and can be used to calculate many useful parameters such as blood flow, volume of distribution, extraction fraction, mean transit time, and standard deviation of transit time as described by Gobbel et al. in "A deconvolution method for evaluating indicator-dilution curves", Physics in Medicine and Biology, Vol. 39, 1833-1854, 1994. From basic physiologic considerations, the expected shape of the tissue impulse response function $R(t)$ is zero until the contrast agent enters the tissue, at which point the tissue impulse response function $R(t)$ achieves its maximum value and then remains constant at this maximum value until the contrast agent begins to leave the tissue. Finally, the tissue impulse response function $R(t)$ returns to zero over a period of time determined by the distribution of transit times of the contrast agent molecules.

In practice, the tissue impulse response function $R(t)$ cannot be observed directly because an ideal bolus of contrast agent cannot be directly injected into the tissue of interest. Rather, a non-ideal bolus of contrast agent is typically introduced into the blood at a location upstream of the tissue of interest. As the contrast agent moves through the blood, the contrast agent concentration is measured by an imaging device, as a function of time, in two locations, one location of which is after the location of injection but upstream of the tissue of interest, $I(t)$, and the other location of which is within the tissue of interest $J(t)$. $J(t)$ represents a combination of both $R(t)$ and $I(t)$, namely the tissue impulse response function whose shape has been complicated by the non-ideality and delay of the bolus. Mathematically, $J(t)$ is the convolution of $R(t)$ and $I(t)$. The effect of a non-ideal $I(t)$ must be corrected in order to calculate $R(t)$ as described by Zierler in "Equations for measuring blood flow by external monitoring of radioisotopes", Circulation Research, Vol. 16, 309-321, 1965. This correction is known as deconvolution.

Given that $I(t)$ and $J(t)$ are both corrupted by noise, the tissue impulse response function can be only estimated as $R'(t)$. There are three major strategies for calculating $R'(t)$, namely Frequency Domain Strategy, Analytical Model Strategy, and Spatial-Domain Strategy. Deconvolution analysis is difficult because it is inherently a differentiating process that is mathematically unstable and therefore very susceptible to noise in either $I(t)$ or $J(t)$ as described by Bronikowski et al. in "Model-free deconvolution techniques for estimating vascular transport function", International Journal of Biomedical Engineering and Technology, Vol. 14, 411-429, 1983. The three strategies have evolved from differing opinions regarding stability of numerical methods.

Deconvolving $I(t)$ from $J(t)$ in the time domain is a difficult and unstable process. Theoretically, deconvolution can be simplified by using Fourier Theory to transform the two functions into their frequency domain counterparts $FI(v)$ and $FT(v)$, where $v$ denotes frequency. The frequency domain counterpart of $R'(t)$, namely $FR'(v)$, can be written as the ratio of $FT(v)$ and $FI(v)$, namely $FR'(v)=FT(v)/FI(v)$. Finally, $FR'(v)$ can be transformed back into the spatial domain to yield $R'(t)$ as described by Alderson et al. in "Deconvolution analysis in radionuclide quantitation of left-to-right cardiac shunts", Journal of Nuclear Medicine, Vol. 20, 502-506, 1979, by Gamel et al. in "Pitfalls in digital computation of the impulse response of vascular beds from indicator-dilution curves", Circulation Research, Vol. 32, 516-523, 1973, by Kuruc et al. in "Accuracy of deconvolution algorithms assessed by simulation studies: Concise Communication", Journal of Nuclear Medicine, Vol. 24, 258-263, 1983 and by Juni et al. in "The appended curve technique for deconvolution analysis—method and validation", European Journal of Nuclear Medicine, Vol. 14, 403-407, 1988.

In practice, the Fast Fourier Transform (FFT) as described by Cooley et al. in "An algorithm for the machine calculation of complex Fourier series", Mathematics of Computation, Vol. 19, 297-301, 1965, and the Inverse FFT are used to move data between the spatial and frequency domains. FFT algorithms assume that $I(t)$ and $J(t)$ are periodic and without discontinuities as described by Wall et al. in "System parameter identification in transport models using the fast Fourier Transform (FFT)", Computers and Biomedical Research, Vol. 14, 570-581, 1980. Unfortunately, significant discontinuities appear if data acquisition is terminated early because of time limitations, while a significant amount of contrast agent remains within the tissue of interest and $J(t)$ has not yet dropped to zero as described in the aforementioned Gobbel et al. reference. Such an abrupt end to $J(t)$, coupled with inherently noisy measurements, produces high-frequency oscillations in the calculated $R'(t)$, as described in the aforementioned Juni et al. reference, that have no underlying physiologic basis as described by Bronikowski et al. in "Model-free deconvolution techniques for estimating vascular transport function", International Journal of Biomedical Engineering and Technology, Vol. 14, 411-429. To address this concern, some authors have developed techniques to temporally extrapolate $I(t)$ and $J(t)$ to zero as described in the aforementioned Gobbel et al., Juni et al. and Wall et al. references; however the validity domain of temporal extrapolations of data has not been fully explored.

The Analytical Model Strategy assumes that the tissue impulse response function can be described by an analytical model that is derived from assumptions about the behavior of the contrast agent within the biological system under investigation as described by Nakamura et al. in "Detection and quantitation of left-to-right shunts from radionuclide angiography using the hormomorphic deconvolution technique", IEEE Biomedical Engineering, Vol. 23, 192-201, 1982, and in the aforementioned Kuruc et al. reference. The analytical model of the tissue impulse response function has parameters that are initially unknown and must be calculated by fitting the model to the data. In general, reducing the number of parameters improves the stability of the model in the presence of noise. Reducing the number of parameters can however, limit the model as the final shape of the tissue impulse response function is restricted to the family of curves that can be realized by manipulating the parameters of the analytical model. The Analytical Model Strategy is a good choice for situations where an analytical model is known to characterize adequately healthy and pathologic tissue. Analytical models work best in specific well-defined biological systems, and should not be used beyond such systems since it is difficult to know a priori the appropriate functional form as described in the aforementioned Juni et al. reference.

The Matrix Strategy is based on an equivalency between discrete convolution and matrix multiplication. The expression $J(t)=I(t) \otimes R'(t)$ can be re-written as $MJ=MI \times MR'$, where ×denotes matrix multiplication; MJ and MR' are vectors representing the I(t) and R'(t) data; and MI is a lower-triangular Toeplitz matrix of the I(t) values. Thus, MR' can be expressed as the solution to this linear set of equations as described by Valentinuzzi et al. in "Discrete deconvolution", Engineering in Medicine and Biology, Vol. 13, 123-125, 1975, by Ham et al. in "Radionuclide quantitation to left-to-right cardiac shunts using deconvolution analysis: Concise Communication", Journal of Nuclear Medicine, Vol. 22, 688-692, 1981, and by Cosgriff et al. in "A comparative assessment of deconvolution and diuresis renography in equivocal upper urinary tract obstructions", Nuclear Medicine Communications, Vol. 3, 377-384, 1982.

The Matrix Strategy has the advantages of neither requiring assumptions of an underlying analytical model nor requiring curves to go to zero. Unfortunately, this strategy can produce widely-oscillating R'(t) that have no physiological significance. To minimize these effects, I(t) and/or J(t) can be pre-processed or R'(t) can be post-processed to reduce their oscillatory nature as described by Basic et al. in "Extravascular background subtraction using deconvolution analysis of the renogram", Physics in Medicine and Biology, Vol. 33, 1065-1073, 1988, and by Gonzalez et al. in "$^{99}Tc^m$-MAG3 renogram deconvolution in normal subjects and in normal functioning kidney grafts", Nuclear Medicine Communications, Vol. 15, 680-684, 1994. Furthermore, R'(t) derived from Matrix Strategy methods can lead to R'(t) having values less than zero, which have no physical significance and must be set to zero as described in the aforementioned Gonzalez et al. reference.

Other contrast agent measurement techniques have also been considered. For example, U.S. Pat. No. 5,135,000 to Akselrod et al. discloses a method of measuring blood flow through tissue in a region of interest. The method includes the steps of injecting an ultrasonic tracer into the blood upstream of the region of interest and also upstream of a specified reference region; utilizing the tracer-produced echo intensity function to compute: (i) the mean transit time of the tracer through the region of interest; and (ii) the blood volume within the region of interest; and dividing the results of computation (ii) by the results of computation (i) to produce a quantitative measurement of the blood flow through the tissue in the region of interest.

The publication entitled "Myocardial Blood Flow Quantification with MRI By Model-Independent Deconvolution" authored by Jerosch-Herold et al. (Physics in Medicine 2002) discloses a method for determining blood flow quantification using model-free deconvolution, the Matrix Strategy and Tikhonov Regularization. The tissue impulse response function is constrained to be a sequence of B-splines (smoothly varying linked polynomial curves). The Matrix Strategy that is employed solves directly for the B-spline coefficients.

U.S. Pat. No. 6,542,769 to Schwamm et al. discloses an imaging system and method for obtaining quantitative perfusion indices. A bolus containing optical and MRI contrast agents is administered to a patient for determining quantitative perfusion indices from perfusion weighted magnetic resonance imaging analysis (PWI). The optical contrast agent time-concentration data, which can be obtained non-invasively, is used to define an arterial input function. The MRI contrast agent time concentration can be non-invasively determined using MRI to define a tissue function. An MRI time-signal curve can be determined by deconvolving the arterial and tissue functions. In one embodiment, SVD is used to determine a residue function from which a flow map can be computed.

U.S. Pat. No. 6,898,453 to Lee discloses a method for determining tissue type using blood flow and contrast agent transit time. Tissue blood flow (TBF) is determined by deconvoluting Q(t) and $C_a(t)$, where Q(t) represents a curve of specific mass of contrast, and $C_a(t)$ represents an arterial curve of contrast concentration, and quantitatively determining a tissue blood volume (TBV) by deconvoluting Q(t) and $C_a(t)$. The method also includes quantitatively determining a tissue mean transit time (TMTT) by deconvoluting Q(t) and $C_a(t)$, and quantitatively determining a tissue capillary permeability surface area product (TPS) by deconvoluting Q(t) and $C_a(t)$. The method also includes determining a tissue type based on the TBF, the TBV, the TMTT, and the TPS.

U.S. Pat. No. 5,287,273 to Kupfer et al. discloses a noninvasive method of determining function of a target organ using a pre-calibrated imaging system. The method contains the steps of introducing an indicator/tracer bolus into the subject's circulatory system and thereafter monitoring simultaneously the responses recorded from the heart/great vessels, and from the target organ. The absolute activity per unit volume of blood withdrawn at a known time(s) is measured, and the observed data from the heart or great vessels is converted into absolute units. These data serve as B(t), the input function. Precalibration of the detector/measuring system allows the observed dynamic indicator/tracer data recorded from the target organ to be expressed in units of absolute activity. These data serve as A(t). A(t) and B(t) are deconvolved in order to obtain the linear response function (LRF), h(t)) for an image element. Functional images of the target organ's LRF are created.

Although contrast measurement techniques exist as is apparent from the above discussion, improvements are desired. It is therefore an object of the present invention at least to provide a novel method and apparatus for quantifying the behaviour of a contrast agent administered to a subject.

SUMMARY OF THE INVENTION

A deconvolution technique for calculating an estimate of the tissue impulse response function, R'(t), of a contrast agent within a tissue is provided. The technique makes use of an imaging device to acquire a time sequence of measurements of the contrast agent before the contrast agent enters the tissue, I(t); and as the contrast agent perfuses the tissue, J(t). I(t) is deconvolved from J(t) to obtain R'(t) using a technique that takes physiologic and physical considerations into account to constrain the shape of R'(t). Two constraints are imposed. First, R'(t) is constrained to have a global minimum of zero or larger at its beginning and end. Second, R'(t) is constrained to have a single local maximum. The location and length of the local maximum can be selected manually, or automatically by the deconvolution technique. The deconvolution technique is based on a modified Matrix Strategy, where deconvolution is formulated in the time domain as a regularized optimization problem.

Accordingly, in one aspect there is provided a method for quantifying contrast agent behavior of an administered contrast agent within a region of interest, comprising: obtaining a time sequence of measurements, I(t), of contrast agent concentration starting before the contrast agent enters the region of interest and a time sequence of measurements, J(t), of the contrast agent concentration as the contrast agent perfuses the region of interest; deconvolving I(t) from J(t) to obtain an estimate of the tissue impulse response function for the region of interest, R'(t), where R'(t) is constrained to take into account at least one of physiologic and physical considerations and is chosen such that I(t)$\otimes$R'(t) is the maximum likelihood estimate of J(t), where $\otimes$ denotes convolution; and determining the behaviour of the contrast agent in the region of interest based on R'(t).

According to another aspect there is provided a method for quantifying contrast agent behavior of an administered contrast agent within a region of interest comprising: obtaining a time sequence of measurements of the contrast agent concentration before the contrast unit enters the region of interest, I(t) and a time sequence of measurements of the contrast agent concentration as the contrast unit perfuses the region of interest, J(t); deconvolving I(t) from J(t) to obtain an estimate of the tissue impulse response function for the region of interest, R'(t), where R'(t) is constrained to have a global minimum of zero or larger at its beginning and end and a single local maximum and is chosen such that I(t)$\otimes$R'(t) is the maximum likelihood estimate of J(t), where $\otimes$ denotes convolution and wherein the location and length of the local maximum of R'(t) is automatically selected using maximum likelihood considerations and R'(t) shape considerations; and determining the behaviour of the contrast agent in the region of interest based on R'(t).

According to yet another aspect there is provided a computer readable medium embodying a computer program for quantifying contrast agent behavior of an administered contrast agent within a region of interest, said computer program comprising: computer program code for causing an imaging device to obtain a time sequence of measurements, I(t), of contrast agent concentration starting before the contrast agent enters the region of interest and a time sequence of measurements, J(t), of the contrast agent concentration as the contrast agent perfuses the region of interest; computer program code for deconvolving I(t) from J(t) to obtain an estimate of the tissue impulse response function for the region of interest, R'(t), where R'(t) is constrained to take into account at least one of physiologic and physical considerations and is chosen such that I(t)$\otimes$R'(t) is the maximum likelihood estimate of J(t), where $\otimes$ denotes convolution; and computer program code for determining the behaviour of the contrast agent in the region of interest based on R'(t).

According to still yet another aspect there is provided an apparatus for quantifying contrast agent behavior of an administrated contrast agent within a region of interest, comprising: an imaging device obtaining a time sequence of measurements, I(t), of contrast agent concentration starting before the contrast agent enters the region of interest and a time sequence of measurements, J(t), of the contrast agent concentration as the contrast agent perfuses the region of interest; and processing structure deconvolving I(t) from J(t) to obtain an estimate of the tissue impulse response function for the region of interest, R'(t), where R'(t) is constrained to take into account at least one of physiologic and physical considerations and is chosen such that I(t)$\otimes$R'(t) is the maximum likelihood estimate of J(t), where $\otimes$ denotes convolution, and determining the behaviour of the contrast agent in the region of interest based on R'(t).

BRIEF DESCRIPTION OF THE DRAWINGS

An embodiment will now be described more fully with reference to the accompanying drawings in which.

DETAILED DESCRIPTION OF THE EMBODIMENTS

Figure 1:
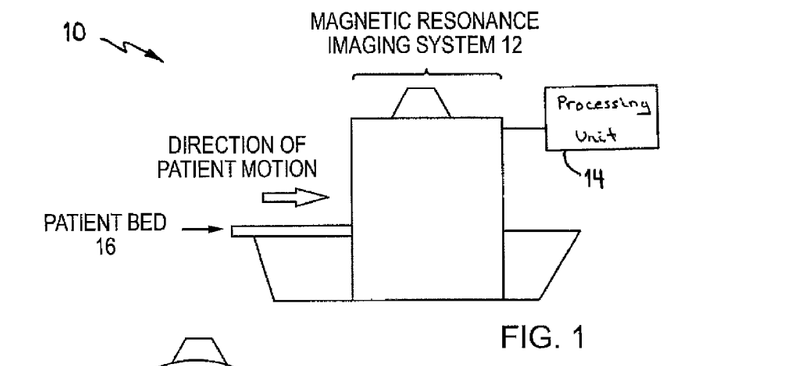
FIG. 1 is a side elevational view of a magnetic resonance imaging system.
Figure 2:
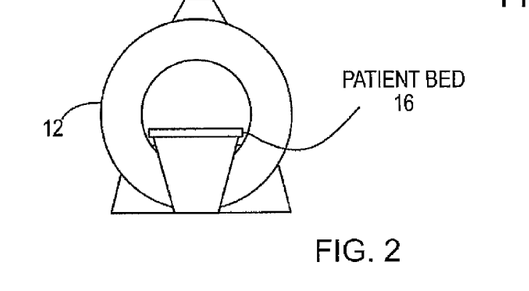
FIG. 2 is an end view of the magnetic resonance imaging system of FIG. 1.

Turning now to FIGS. 1 and 2, a contrast agent behaviour determining apparatus is shown and is generally identified by reference numeral 10. As can be seen, apparatus 10 comprises an imaging device, in this embodiment a magnetic resonance imaging (MRI) system 12 coupled to a processing unit 14 such as for example a personal computer (PC). MRI system 12 is conventional and comprises a bed 16 on which a subject who has been injected with a contact agent lies. Images acquired by the MRI system 12 are conveyed to the processing unit 14 and the image data is processed in a manner that allows the behaviour of the administered contrast agent to be quantified. In particular, the processing unit 14 executes program code to employ a deconvolution technique that is based on a modified Matrix Strategy, where deconvolution is formulated in the time domain as a regularized optimization problem and that takes physiologic and physical considerations into account.

Figure 3:
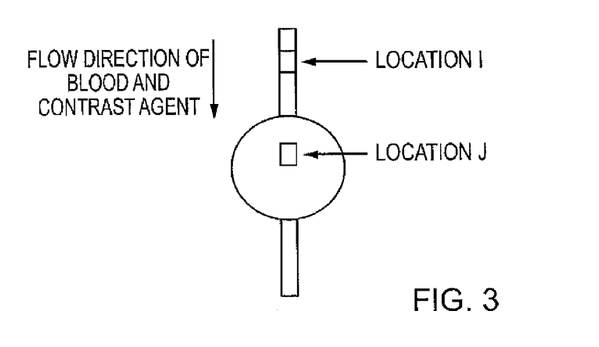
FIG. 3 shows locations at which time sequences of images are acquired.
Figure 4A:
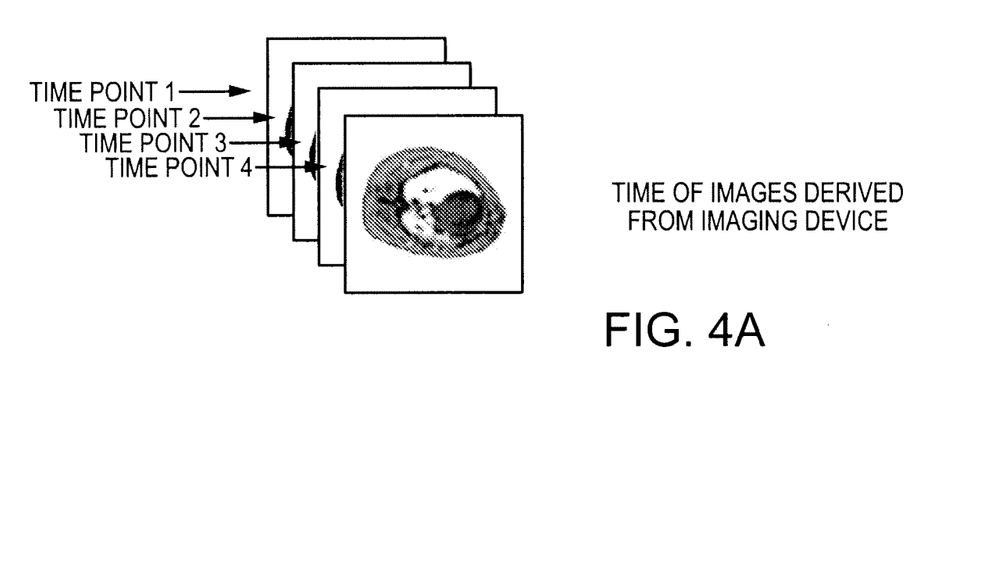
FIG. 4A shows a time sequence of images derived from the magnetic resonance imaging system of FIG. 1.
Figure 4B:
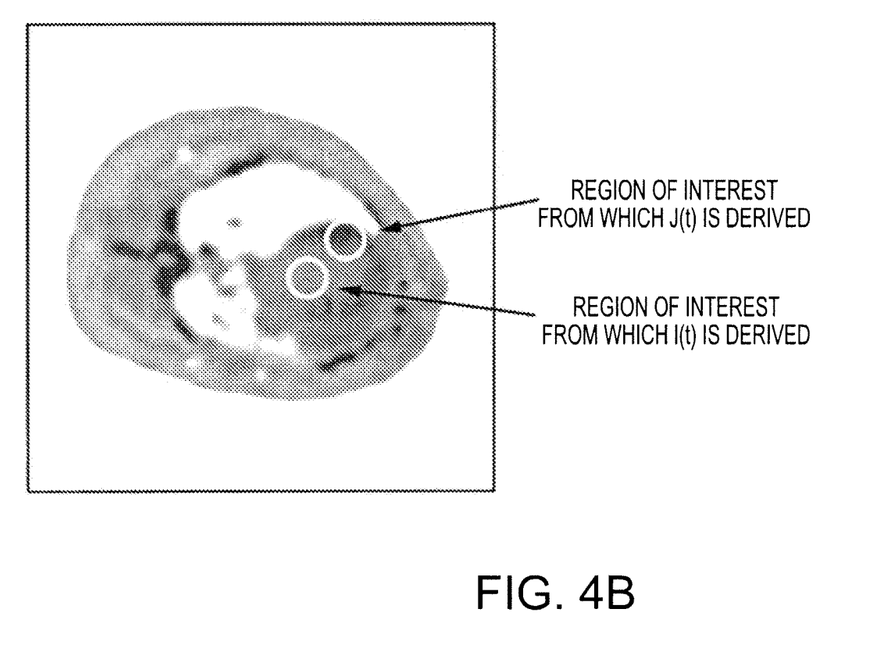
FIG. 4B shows regions of interest from which J(t) and I(t) are derived.

In general, during operation with the subject lying on the bed 16 and having been injected with the contrast agent, the MRI system 12 is operated so that it acquires a time sequence of images at two tissue locations of the subject, one tissue location I of which is outside of the region of interest (ROI) of the subject to be imaged and the other tissue location J of which is within the ROI (see FIGS. 3 and 4A). The acquired images measure the spatio-temporal distribution of the contrast agent within the subject. Thus, the time sequence of images at location I detect the contrast agent before the contrast agent enters the ROI and the time sequence of images at location J detect the contrast agent as the contrast agent perfuses the ROI. The acquired images are then applied to the processing unit 14 which in turn processes the image data to derive J(t) and I(t) as shown in FIG. 4B. Derived J(t) and I(t) are then used to determine a vector MR' describing the discrete time estimate of the tissue impulse response function (TIRF) thereby to enable the behaviour of the administrated contrast agent to be quantified.

In particular, during processing I(t) is deconvolved from J(t) to obtain MR' using a technique that takes physiologic and physical consideration into account to constrain the shape of MR'. Firstly, MR' is constrained to have a global minimum of zero or larger at its beginning and end and secondly MR' is constrained to have a single local maximum. The location and the length of the local maximum can be user selected or automatically selected by the processing unit 14. Further specifies of the processing of the acquired images to determine vector MR' will now be described.

J(t) is defined by Equation [E-1] below as:

$$J(t) = I(t) \otimes R(t) = \int_0^t I(t-\xi) R(\xi) d\xi, \qquad [\text{E-1}]$$

where:
t is a continuous variable of time; and
⊗ denotes convolution.

However, in practice, I(t) and J(t) are measured at discrete points in time at intervals of Δt, for a total of N measurements each. Using zero-order numerical integration, Equation [E-1] is commonly approximated as a discrete-time convolution according to Equation [E-2] below:

$$J(n \cdot \Delta t) = \sum_{m=1}^{N} I(n \cdot \Delta t - m \cdot \Delta t) R(m \cdot \Delta t) \Delta t. \qquad [\text{E-2}]$$

Without loss of generality, herein it is assumed that Δt=1, recognizing that the time interval between points in R'(t) will be the same as the original interval at which I(t) and J(t) were sampled.

The following variables are introduced:

MI is a vector describing the discrete time measurements of I(t), with elements $mi_x$, where x=1, 2, ..., N;

MJ is a vector describing the discrete time measurements of J(t), with elements $mj_x$, where x=1, 2, ..., N;

MR' is a vector describing the discrete time function R(t), with elements $mr_x$, where x=1, 2, ..., N;

MR' is a vector of describing the discrete time estimate of the tissue impulse response function, with elements $mr'_x$, where x=1, 2, ..., N; and TMI is the lower triangular Toeplitz matrix of MI elements. These variables allow Equation [E-2] to be recast as Equation [E03] below:

$$\begin{bmatrix} mj_1 \\ mj_2 \\ mj_3 \\ \dots \\ mj_N \end{bmatrix} = \begin{bmatrix} mi_1 & 0 & 0 & \dots & 0 \\ mi_2 & mi_1 & 0 & \dots & 0 \\ mi_3 & mi_2 & mi_1 & \dots & 0 \\ \dots & \dots & \dots & \dots & \dots \\ mi_N & mi_{N-1} & mi_{N-2} & \dots & mi_1 \end{bmatrix} \times \begin{bmatrix} mr_1 \\ mr_2 \\ mr_3 \\ \dots \\ mr_N \end{bmatrix}, \qquad [\text{E-3}]$$

or more compactly as Equation [E-4] below:

$$MJ = TMI \times MR, \qquad [\text{E-4}]$$

where:
×denotes matrix multiplication.

The goal is to find an MR' such that TMI×MR' is the maximum likelihood estimate of MJ. The maximum likelihood estimate is dependent upon the noise properties of the measured data. Here, the specific case of maximum likelihood estimates associated with the Poisson probability density function are considered; however, other probability density functions can of course be considered. For example, the Rician probability density function may be used.

Thus, if MI and MJ are subject to Poisson statistics, the maximum likelihood estimate is the objective function expressed by Equation [E-5] below:

$$\max \Sigma [MJ \cdot \log(TMI \times MR') - TMI \times MR'], \qquad [\text{E-5}]$$

where:
·denotes element-by-element multiplication.

TMI is poorly conditioned in practice and thus, there are many MR' that satisfy Equation [E-5] almost equally well. Having identified this indeterminacy, additional conditions are imposed on the family of solutions to Equation [E-5] in order to select a preferred MR'. These conditions are defined by linear inequality constraints. In this embodiment, three (3) linear inequality constraints on Equation [E-5] are introduced to account for the physical and physiological considerations discussed earlier. The first linear inequality constraint ensures the first and last elements of MR' are zero or larger and is expressed by Equation [E-6] below:

$$L1 \times MR' \geq 0, \qquad [\text{E-6}]$$

where:
L1 is a 2×N matrix with the first element on the first row being one (1), the last element on the second row being one (1), and the other elements being zero (0).

Similarly, the second and third linear inequality constrains act together to ensure MR' has a single local maximum by enforcing a first derivative greater than zero prior to the maximum and a first derivative less than zero after the local maximum. These linear inequality constraints can be written as Equations [E-7] and [E-8] below:

$$L2 \times MR' \geq 0, \qquad [\text{E-7}]$$

and $$L3 \times MR' \geq 0, \qquad [\text{E-8}]$$

where:
L2 and L3 are numerical differentiation matrixes using Richardson's Extrapolation. L2 is a P×N matrix where P is the starting location of the local maximum of MR', and P<N; and it constrains MR' elements $mr_x$ for x≤P. The L3 restriction operates for x>P.

Finally, the length of the local maximum is specified via Equation [E-9] below:

$$L4 \times MR' = 0, \qquad [\text{E-9}]$$

where:

L4 is a matrix with diagonal elements comprised of P-1 zeros (0), PL ones (1), and N−(P−1+PL) zeros (0), and super-diagonal elements of P-1 zeros (0), PL minus ones (−1), and N−(P−1+PL)−1 zeros (0);

P is the starting location of the local maximum; and

PL is the length of the local maximum.

In the case of the local maximum length being automatically specified, the constraint of Equation [E-9] is not used.

Having defined the variables and functions, the preferred MR' can be expressed as that which solves Equation [E-10] below:

$$\max\{\Sigma[MJ \cdot \log(TMI \times MR') - TMI \times MR']\}$$

subject to both $$\begin{bmatrix} L1 \\ L2 \\ L3 \end{bmatrix} \times MR' \geq 0 \quad [\text{E-10}]$$

and $$L4 \times MR' = 0.$$

The deconvolution technique employed by the processing unit 14 is based on four notable assumptions concerning the properties of the contrast agent, the imaging system and the physiologic behavior of the biological system under interrogation.

The first assumption is that of stationarity (or time-invariance), which is required for the validity of the convolution and deconvolution operations as described in the aforementioned Gonzalez et al. reference. It is assumed that the characteristic behavior of the contrast agent and the tissue do not change during the course of the data acquisition by the MRI system 12.

The second assumption is that vectors MI are MJ are accurately known. In practice, the anatomic region where MI is measured should be in close proximity to the anatomic region where MJ is measured. Referring to FIG. 3, if location I is too far upstream from location J, then the contrast agent will become spatially dispersed prior to entering the tissue at location J, and MI will not accurately represent the true distribution of contrast agent before it enters the tissue as described in the aforementioned Bassingthwaigthe et al. and Gobbel et al. references. The subject deconvolution technique, however, accounts for spatial dispersion by allowing MR' to begin before its local maximum, and has freedom in how it increases to that local maximum. The size of location I should also be small, since measurements over large regions will temporally smooth MI thus decreasing the accuracy of MR'. The second assumption also requires that the MRI system 12 be capable of making accurate measurements of the concentration of the contrast agent. In practice, this may require corrections for contaminating signals and effects of limited spatial resolution.

The third assumption concerns contrast agent re-circulation. Referring to FIG. 3, it is assumed that the contrast agent passes through location I and subsequently through location J, and that no part of the contrast agent enters location J without first passing through location I. If the contrast agent re-circulates after leaving location J, then any contrast agent molecules that enter location J for the second time have first passed through location I a second time. This assumption forms the basis for constraining MR' to have a single local maximum.

The fourth assumption is that the system under observation is linear as described in the aforementioned Juni et al. and Gonzalez et al. references. That is, an increase in injected contrast agent concentration will result in the same relative increase in the observed contrast agent concentration. This situation does not exist for some contrast agents administered at high levels, where receptors or transport mechanisms may become saturated. However, for most medical imaging device contrast agents, the contrast agents are administered at doses low enough to avoid saturation effects.

Although the embodiment described above makes reference to magnetic resonance imaging and nuclear medicine, those of skill in the art will appreciate that the subject method for estimating a tissue impulse response function has applications in many areas of medical research, routine clinical practice, and pharmaceutical research. For example, the subject deconvolution technique could be applied to a situation where a medical imaging device has acquired a single I(t) and multiple J(t)'s, each corresponding to a single pixel in an image. Repeated application of the tissue impulse response function method allows for the calculation of a set of R'(t)'s, each corresponding to the J(t)'s, and thus producing a map of contrast agent kinetic parameters across the image. Also, although the use of maximum likelihood techniques provided for the case of measurement errors following a Poisson distribution is described, those of skill in the art will appreciate that other measurement errors exist such as constant variance distributions.

As mentioned above, other imaging devices besides magnetic resonance imaging systems may be used. For example, the imaging device may be a gamma camera, a magnetic resonance spectroscopy system, an ultrasound imaging system, an optical imaging system, a positron emission tomography system, a hybrid imaging device, a combined gamma camera/X-ray computed tomography system, a combined positron emission tomography/X-ray computed tomography system and a combined magnetic resonance imaging/positron emission tomography

EXAMPLES

The most promising MRI technique for perfusion assessment and ischemia detection is rapid MRI of the heart following a bolus injection of a MRI contrast agent, followed by quantitative kinetic analysis of the contrast agent during first pass as described by Wilkie et al. in "Magnetic resonance first-pass myocardial perfusion imaging: Clinical validation and future applications", Journal of Magnetic Resonance Imaging, Vol. 10, 676-686, 1999. Kinetic analysis often involves compartmentalized modeling, where constraints improve numerical stability but can compromise accuracy and assumptions may break down in pathological conditions as described by Jerosch-Herold et al. in "Myocardial blood flow quantification with MRI by model-independent deconvolution", Physics in Medicine, Vol. 29, 886-897, 2002. Computer simulations were performed to test the ability of the subject deconvolution technique to estimate perfusion over a clinically relevant range (1-4 ml/min/g) at clinical noise levels (20:1 contrast-to-noise). Three volunteers underwent dynamic MRI after contrast agent injection, at rest (n=3) and maximal vasodilation (n=2). The volunteers were injected with MRI contrast (Gd-DTPA, 0.04 mmol/kg, 7 ml/s power injected, 10 ml saline flush), and T1-MRI (fast gradient echo sequence, 3 short-axis 8 mm thick slices) acquired for 50 heartbeats to track the contrast agent through first pass and recirculation. Scans were acquired at rest and, for two volunteers, scans were also acquired at adenosine-induced maximal vasodilation. Cardiac perfusion was calculated using both the subject deconvolution technique and clinical software implementing the method described in the aforementioned Jerosch-Herold et al. reference, the content of which is incorporated herein by reference. One hundred (100) noise realizations were produced for each perfusion level.

Figure 5A:
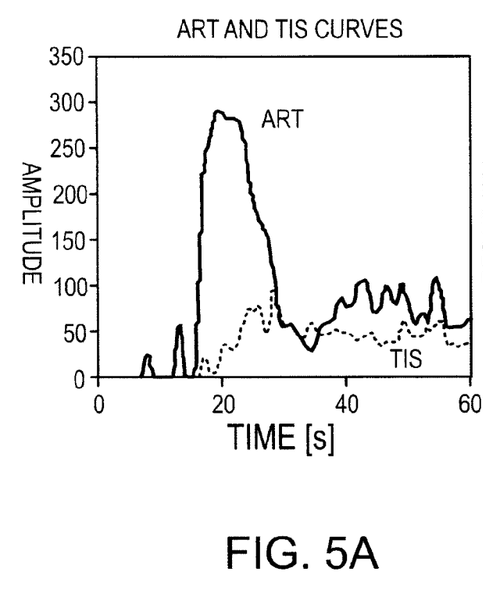
FIG. 5A shows contrast agent concentration vs time curves for blood pool (ART) and tissue (TIS)
Figure 5B:
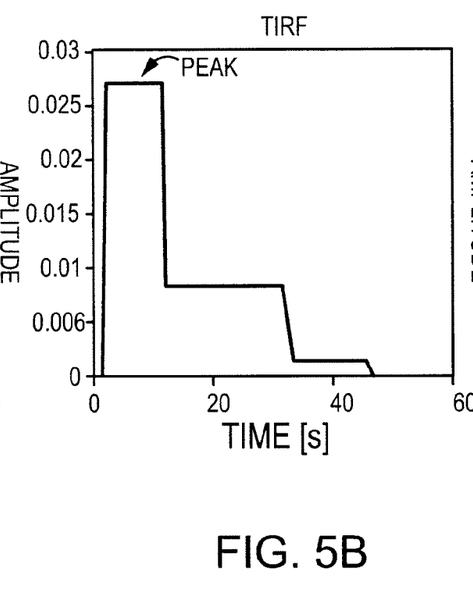
FIG. 5B shows the tissue impulse response residue function (TIRF)
Figure 5C:
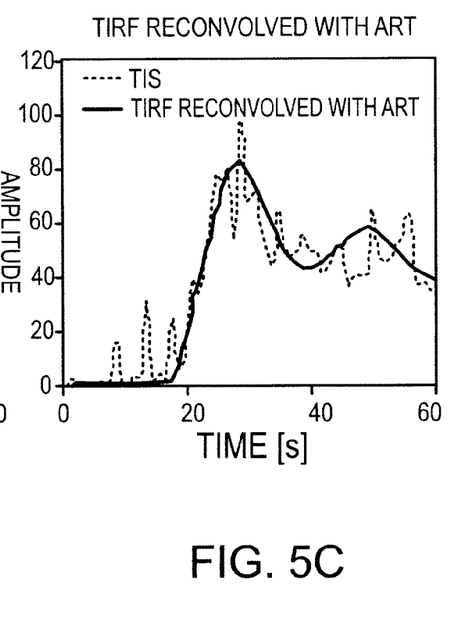
FIG. 5C shows the TIRF of FIG. 5B reconvolved with the ART of FIG. 5A.

As described above, the subject deconvolution technique employed for kinetic analysis of contrast MRI is based on the central volume principle, which requires calculation of the tissue impulse residue function (TIRF). The maximum of the TIRF is defined as the tissue perfusion. TIRF is calculated by recording the contrast agent concentration curve at the point of entry into a region of interest (arterial curve) and the contrast agent concentration curve at the tissue of interest, and then deconvolving the arterial curve from the tissue curve. In this example, the subject deconvolution technique explicitly considers the Rician noise distribution in MR data and (ii) the shape of the TIRF curve has only two constraints, namely a constraint based on physical considerations TIRF must be >=0 at its beginning and end, and (ii) a constraint based on physiologic considerations (TIRF has only a single local maximum). The shape of the TIRF curve is not otherwise constrained The physical and physiologic constrains are expressed as linear inequality constraints. The TIRF is calculated iteratively using a maximum-likelihood objective function incorporating the Rician noise model as described by Sijbers et al. in "Maximum-Likelihood Estimation of Rician Distribution Parameters", IEEE Transactions on Medical Imaging, Vol. 17, 357-361, 1998. The regions of interest are drawn on a short-axis dynamic cardiac MRI corresponding to blood pool and myocardium (not shown). FIG. 5A shows contrast agent concentration vs time curves for blood pool (ART), and tissue (TIS). FIG. 5B shows the TIRF calculated by the subject deconvolution technique. The TIRFs fall naturally into a step-like appearance, where the peak amplitude corresponds to tissue perfusion according to the central volume principle. The delay in peak presentation indicates the contrast agent's transit time between ART and TIS, the finite rise time is indicative of contrast agent dispersion between ART and TIS, the length of the plateau indicates the contrast agent's minimum transit time within TIS. FIG. 5C shows TIRF reconvolved with ART, indicating the quality of the deconvolution and goodness of fit.

Figure 6A:
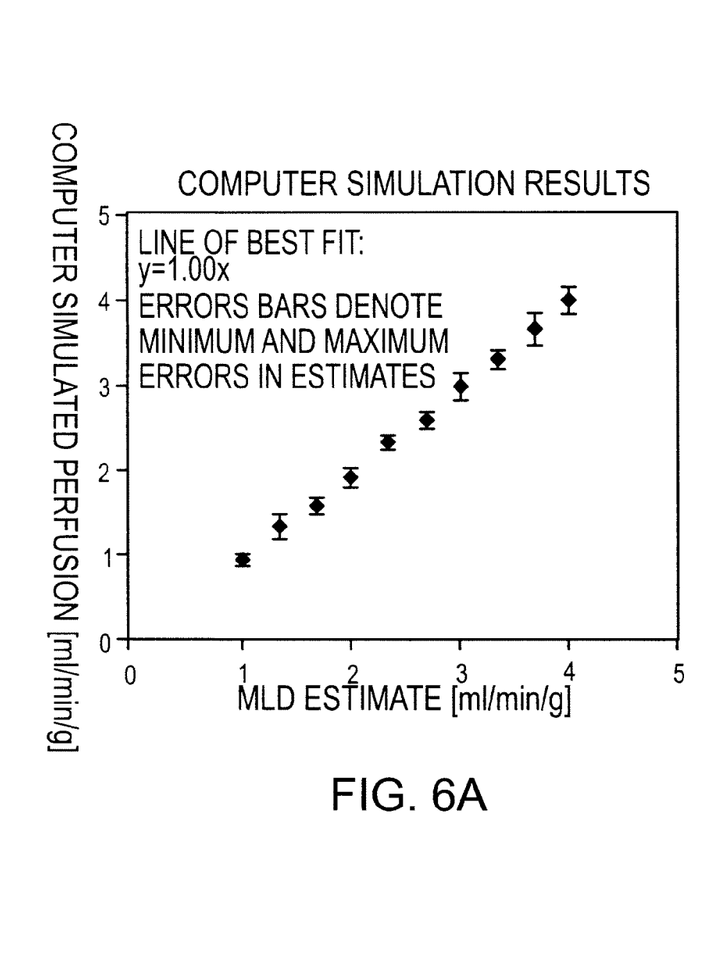
FIGS. 6A and 6B show computer simulation and clinical evaluation results.

Form the computer simulations, synthetic TIRF curves were constructed corresponding to the range of perfusions observed clinically (1-4 ml/min/g), convolved with a clinically measured ART curve, and noise was added (contrast-to-noise 20:1 i.e. a typical clinical level). The results shown in FIG. 6A demonstrate correlation between simulated perfusion levels and the calculated estimates.

Figure 6B:
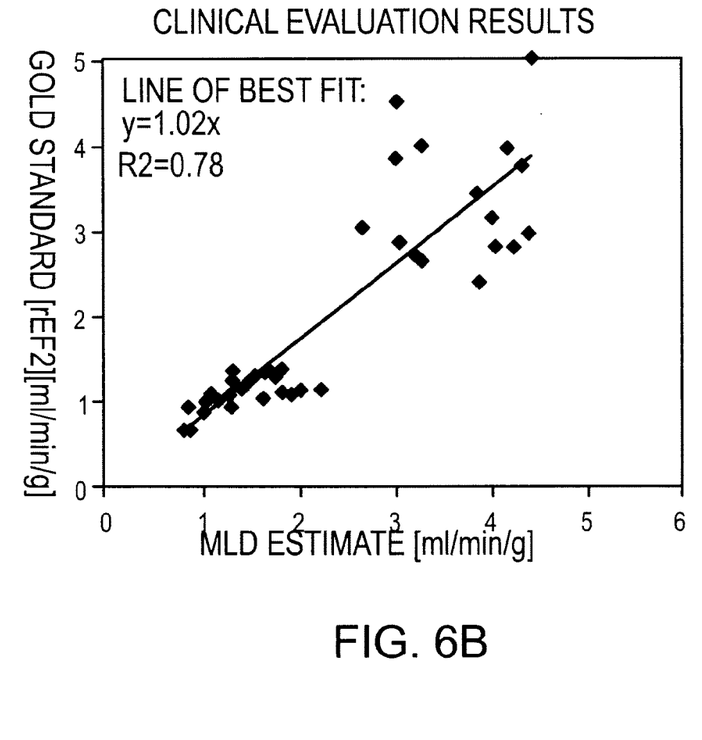

Blood pool and tissue regions-of-interest were defined, from which ART and TIS curves were generated. For ART curves a region of interest was defined in the centre of the left ventricle. For TIS curves Endo- and epicardial contours were traced manually, divided into 8 transmural equicircumferential sectors. Perfusion was calculated two ways, namely using the technique of the above-incorporated Jerosch-Herold et al. reference (gold standard), and the subject deconvolution technique. The results shown in FIG. 6B demonstrate general agreement between the gold standard and the subject deconvolution technique ($R^2=0.78$). The simulations demonstrate that the subject deconvolution technique is numerically stable and accurately estimates perfusion at clinical contrast:noise levels for typical cardiac perfusion values. Theoretically, the subject deconvolution technique estimates of perfusion are expected to be unbiased, and have minimum variance (achieving the Cramer-Rao bound). The subject deconvolution technique estimates of perfusion are similar to estimates provided by a widely used clinical perfusion package. Previous deconvolution techniques stabilized deconvolution via smoothing penalty functions or constraining TIRFs to smooth piece-wise functions (such as splines). Using the subject deconvolution technique these constraints are removed, and interestingly, the TIRFs appear step-like, which may indicate discrete capillary populations with differing transit times. The subject deconvolution technique intrinsically models dispersion of the contrast agent between the arterial and tissue curves, which is not accounted for by the clinical package and may partially explain discrepancies.

The program code executed by the processing unit may comprise program modules including but not limited to routines, programs, object components, data structures etc. and may be embodied on a computer readable medium. The computer readable medium is any data storage device that can store data, which can thereafter be read by a computer system. Examples of computer readable medium include for example read-only memory, random-access memory, flash memory, CD-ROMs, magnetic tape, optical data storage devices and other storage media. The computer readable program code can also be distributed over a network including coupled computer systems so that the computer readable program code is stored and executed in a distributed fashion or copied over a network for local execution.

Although preferred embodiments have been described with reference to the drawings, those of skill in the art will appreciate that variations and modifications may be made without departing from the spirit and scope thereof as defined by the appended claims.

What is claimed is:

1. A non-transitory computer readable medium embodying a computer program that when executed by a processing unit, at least causes the processing unit to quantify contrast agent behavior of an administered contrast agent within a region of interest of a subject, said computer program comprising:

computer program code for processing image data of an acquired time sequence of images including two tissue locations, one of said tissue locations (I) being outside of said region of interest and the other of said tissue locations (J) being within said region of interest, to yield a time sequence of measurements, I(t), at the tissue location (I) outside of the region of interest that detect contrast agent concentration before the contrast agent enters the region of interest and to yield a time sequence of measurements, J(t), at the tissue location (J) within the region of interest that detect the contrast agent concentration as the contrast agent perfuses the region of interest;

computer program code for deconvolving I(t) from J(t) to determine a vector describing the time estimate of the impulse response function, R'(t), for the region of interest, where the shape of the vector is constrained such that the vector comprises a single local maximum and such that first and last elements of said vector have values no less than zero; and computer program code for determining the behaviour of the contrast agent in the region of interest based on the determined vector, wherein the two tissue location (I) and (J) are in close proximity to avoid spatial dispersion of the contrast agent prior to entry into the region of interest and wherein tissue location (I) is small to avoid smoothing of the time sequence of measurements I(t).

2. An apparatus for quantifying contrast agent behavior of an administrated contrast agent within a region of interest of a subject, comprising:
   an imaging device configured to acquire a time sequence of images of a subject including two tissue locations, one of said tissue locations (I) being outside of said region of interest and the other of said tissue locations (J) being within said region of interest; and
   a processing unit communicating with said imaging device, said processing unit configured to process image data of said acquired images to yield a time sequence of measurements, I(t), at the tissue location (I) outside of the region of interest that detect contrast agent concentration before the contrast agent enters the region of interest and to yield a time sequence of measurements, J(t), at the tissue location (J) within the region of interest that detect the contrast agent concentration as the contrast agent perfuses the region of interest, said processing unit further configured to deconvolve I(t) from J(t) to determine a vector describing the time estimate of the impulse response function, R'(t), for the region of interest, where the shape of the vector is constrained such that the vector comprises a single local maximum and such that first and last elements of said vector have values no less than zero, and to determine the behaviour of the contrast agent in the region of interest based on the determined vector, wherein the two tissue location (I) and (J) are in close proximity to avoid spatial dispersion of the contrast agent prior to entry into the region of interest and wherein tissue location (I) is small to avoid smoothing of the time sequence of measurements I(t).

3. An apparatus according to claim 2 wherein said imaging device comprises one of a gamma camera, a magnetic resonance imaging system, a magnetic resonance spectroscopy system, an ultrasound imaging system, an optical imaging system, a positron emission tomography system, and a hybrid imaging device.

4. An apparatus according to claim 2 wherein said imaging device comprises one of a combined gamma camera/X-ray computed tomography system, a combined positron emission tomography/X-ray computed tomography system, and a combined magnetic resonance imaging/positron emission tomography system.

5. An apparatus according to claim 2 wherein said processing unit is further configured to calculate blood flow and blood volume from the vector.

6. An apparatus according to claim 2 wherein said processing unit is further configured to constrain a length of said single local maximum.

7. An apparatus according to claim 6 wherein said processing unit is configured to select the location and length of the local maximum of vector either automatically or in response to user input.

8. An apparatus according to claim 2 wherein said imaging device comprises one of a gamma camera, a magnetic resonance imaging system, a magnetic resonance spectroscopy system, an ultrasound imaging system, an optical imaging system, a positron emission tomography system, and a hybrid imaging device.

9. An apparatus according to claim 2 wherein said imaging device comprises one of a combined gamma camera/X-ray computed tomography system, a combined positron emission tomography/X-ray computed tomography system, and a combined magnetic resonance imaging/positron emission tomography system.

10. An apparatus according to claim 2 wherein said processing unit is configured to process image data of acquired images to yield I(t) and J(t) for a plurality of regions of interest, for each region of interest said processing structure configured to deconvolve I(t) from J(t) to determine the vector describing the time estimate of the impulse response function, R'(t), for the region of interest and determine the behaviour of the contrast agent in the region of interest based on the determined vector.

11. An apparatus according to claim 10 wherein said processing unit is configured to select the location and length of the local maximum of vector either automatically or in response to user input.

12. An apparatus according to claim 10 wherein said processing unit is further configured to calculate blood flow and blood volume from the vector.

* * * * *